US011040943B2

(12) United States Patent
Vaino et al.

(10) Patent No.: US 11,040,943 B2
(45) Date of Patent: *Jun. 22, 2021

(54) PSYCHOTROPIC AGENTS AND USES THEREOF

(71) Applicant: LB PHARMACEUTICALS INC., New York, NY (US)

(72) Inventors: Andrew R. Vaino, New York, NY (US); Vincent T. Grattan, New York, NY (US); Zachary Prensky, New York, NY (US)

(73) Assignee: LB Pharmaceuticals Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/561,767

(22) Filed: Sep. 5, 2019

(65) Prior Publication Data

US 2020/0002277 A1 Jan. 2, 2020

Related U.S. Application Data

(63) Continuation of application No. 16/383,933, filed on Apr. 15, 2019, now abandoned, which is a continuation of application No. 15/824,966, filed on Nov. 28, 2017, now Pat. No. 10,259,786.

(60) Provisional application No. 62/427,062, filed on Nov. 28, 2016, provisional application No. 62/508,263, filed on May 18, 2017.

(51) Int. Cl.
| | |
|---|---|
| *C07D 207/09* | (2006.01) |
| *C07C 317/36* | (2006.01) |
| *A61P 25/18* | (2006.01) |
| *A61K 45/06* | (2006.01) |
| *A61K 31/166* | (2006.01) |
| *A61K 31/40* | (2006.01) |

(52) U.S. Cl.
CPC .......... *C07D 207/09* (2013.01); *A61K 31/166* (2013.01); *A61K 31/40* (2013.01); *A61K 45/06* (2013.01); *A61P 25/18* (2018.01); *C07C 317/36* (2013.01)

(58) Field of Classification Search
CPC .... C07D 207/09; C07C 317/36; A61K 45/06; A61K 31/166; A61K 31/40; A61P 25/18
See application file for complete search history.

(56) References Cited

U.S. PATENT DOCUMENTS

| | | | |
|---|---|---|---|
| 4,210,660 A | 7/1980 | Takashima et al. | |
| 4,401,822 A * | 8/1983 | Thominet | C07D 207/09 548/567 |
| 4,772,630 A | 9/1988 | Storni et al. | |
| 5,686,482 A | 11/1997 | Ohmori et al. | |
| 6,069,165 A | 5/2000 | Andrieu et al. | |
| 6,169,094 B1 | 1/2001 | Perrault et al. | |
| 8,394,790 B2 | 3/2013 | Portnoy et al. | |
| 8,828,993 B2 | 9/2014 | Portnoy et al. | |
| 10,259,786 B2 | 4/2019 | Vaino et al. | |

FOREIGN PATENT DOCUMENTS

| | | |
|---|---|---|
| EP | 0757985 A1 | 2/1997 |
| JP | 2002-520370 | 7/2002 |
| WO | 95/29891 A1 | 11/1995 |
| WO | 00/03740 | 1/2000 |
| WO | 2012/062697 A1 | 5/2012 |
| WO | 2018/098497 A1 | 5/2018 |
| WO | 2018/213813 A8 | 11/2018 |
| WO | 2019/113079 A1 | 6/2019 |

OTHER PUBLICATIONS

Abbas, A.A. et al. "Amisulpride Is a Potent 5-Ht7 Antagonist: Relevance for Antidepressant Actions In Vivo", Psychopharmacology, 2009, 119-128.

CNN, "FDA mulls drug to slow late-stage Alzheimer's" [online], [retrieved on Sep. 23, 2003] Retrieved from the Internet. URL: http//www.cnn.com/2003/HEALTH/conditions/09/24/alzheimers.drug.ap/indexhtml>. 2 pages.

Damasio, A. "Alzheimer's Desease and Related Dementias" Cecil Textbook of Medicine, 20th Edition (1996), vol. 2, pp. 1992-1996.

Donahue "Characterization of the Discriminative Stimulus Properties of the Atypical Antipsychotic Amisulpride in C57BL/6 Mice" Virginia Commonwealth University. Dec. 2, 2014, pp. 1-131.

Donahue, T., et al. "Discriminative stimulus properties of the atypical antipsychotic amisulpride: comparison to its isomers and to other benzamide derivatives, antipsychotic, antidepressand, and antianxiety drugs in C57BL/6 mice" Psychopharmacology, Sep. 2017, vol. 234, No. 23, pp. 3507-3520.

(Continued)

*Primary Examiner* — Sikarl A Witherspoon
(74) *Attorney, Agent, or Firm* — Perkins Coie, LLP

(57) ABSTRACT

Novel amisulpride derivatives and pharmaceutical compositions thereof are disclosed. The amisulpride derivative disclosed herein or a pharmaceutical composition thereof may have better membrane permeability compared to amisulpride. The amisulpride derivative disclosed herein or a pharmaceutical composition thereof may be used for antagonizing dopamine and/or serotonin (e.g., 5-HT2a) and/or α2 receptor in a subject, either individually or in combination with other CNS active agents. The amisulpride derivative disclosed herein or a pharmaceutical composition thereof may be used for treating one or more conditions responsive to modulation of dopamine and/or serotonin (e.g., 5-HT2a) and/or α2 receptor in a subject, either individually or in combination with other CNS active agents. The amisulpride derivative disclosed herein or a pharmaceutical composition thereof may be used for treating one or more disorders associated with an abnormality in levels of dopamine and/or serotonin in the brain, either individually or in combination with other CNS active agents.

21 Claims, 3 Drawing Sheets

(56) References Cited

OTHER PUBLICATIONS

Dorwald, F.Z. Side Reactions in Organic Synthesis, 2005, Wiley-VCH Verlag GmbH & Co. KGaA, Weinheim, Preface. p. IX. (2005).
Dos Santos Pereira, J.N., et al. "The Poorly Membrane Permeable Antipsychotic Drugs Amisulpride and Sulpride Are Substrates of the Organic Cation Transporters from the SLC22 Family", The AAPS Journal, 2014, 16, 1247-1258.
EPO, Extended European Search Report for European Patent Application No. 17873556.9. dated Nov. 18, 2019. 12 pages.
Guzman, F. "Serotonin (5-HT): receptors, agonist and antagonists" [online], [retrieved on Apr. 30, 2018]. Retrieved from the Internet, URL: http://pharmacologycorner.com/serotonin-5ht-recptors-agonists-antogonist/. 6 pages.
Iwanami, S., et al. "Synthesis and Neuroleptic Activity of Benzamides. Cis-N-(1-Benzyl-2-methylpyrrolidin-3-yl)-5-chloro-2-methoxy-4-(methylamino)benzamide and Related Compounds" J. Med. Chem. 1981, vol. 24, pp. 1224-1230.
Jafari, S. et al. "Structural Contributions of Antipsychtoic Drugs to Their Therapeutic Profiles and Metabolic Side Effects", J. Neurochemistry, 2012, 120, 371-384.
Joyce, J.J. et al. "Linking the Family of D2 Receptors to Neuronal Circuits in Human Brain: Insights Into Schizophrenia", Neuropsychopharmacology, 1997, 16, 1444-1449.
Layzer, R. "Section Five—Degenerative Diseases of the Nervous System" Cecil Textbook of Medicine, 20th Edition (1996), vol. 2, pp. 2050-2057.
Meltzer, H.Y. et al. "The Dopamine Hypothesis of Schizophrenia—A Review", Schizophr. Bull., 1976, 2, 19-76.
Neill, J.C., et al. "Acute and Chronic Effects of Nmda Receptor Antagonists in Rodents, Relevance to Negative Symptoms of Schizophrenia: A Translational Link to Humans", European Neuropsychopharmacology, 2014, 24, 822-835.
Neill, J.C., et al. "Animal Models of Cognitive Dysfunction and Negative Symptoms of Schizophrenia: Focus on NMDA Receptor Antagonism", Pharmacology & Therapeutics, 2010, 128, 419-432.
Neill, J.C., et al. "Effects of Cariprazine, A Novel Antipsychotic, on Cognitive Deficit and Negative Symptoms in a Rodent Model of Schizophrenia Symptomatology", European Neuropsychopharmacology, 2016, 26, 3-14.
Rosenzweig, P., et al. "A review of the pharmacokinetics, tolerability and pharmacodynamics of amisulpride in healthy volunteers" Clinical and Experimental Human Psychopharmacology, vol. 17, No. 1, pp. 1-13.
Roth, B.L., et al. "Magic Shotguns Versus Magic Bullets: Selectively Non-Selective Drugs for Mood Disorders and Schizophrenia", Nature Reviews Drug Discovery, 2004, 3, 353-359.
Shoemaker, H., et al. "Neurochemical Characteristics of Amisulpride, An Atypical Dopamine D2/D3Receptor Antagonist With Both Presynaptic and Limbic Selectivity", J. Pharmacol. Exp. Ther., 1997, 280, 83-97.
USPTO, International Preliminary Report on Patentability for International Application No. PCT/US17/63529, dated Jun. 6, 2019. 7 pages.
USPTO, International Search Report and Written Opinion for International Application No. PCT/US17/63529, dated Feb. 26, 2018. 9 pages.
USPTO, International Search Report and Written Opinion for International Application No. PCT/US18/33552, dated Aug. 13, 2018. 13 pages.
USPTO, Non-Final Office Action for U.S. Appl. No. 15/824,966, dated May 4, 2018. 26 pages.
USPTO, Non-Final Office Action for U.S. Appl. No. 15/896,851, dated May 3, 2018. 16 pages.
USPTO, Notice of Allowance for U.S. Appl. No. 15/824,966, dated Nov. 23, 2018. 23 pages.
USPTO, Notice of Allowance for U.S. Appl. No. 15/896,851, dated Sep. 6, 2018. 18 pages.
USPTO, Non-Final Office Action for U.S. Appl. No. 16/561,829, dated Dec. 6, 2019. 9 pages.
Wulff, S., et al. "Striatal D2/3 Binding Potential Values in Drug-Naïve First-Episode Schizophrenia Patients Correlate With Treatment Outcome", Schizophrenia Bulletin, 2015, 41, 1143-1152.
Japanese Office Action for 2019-548535 dated Jul. 14, 2020, with translation, 10 pages.
Shinji Usuda, "Anti-dopaminergic Activity of Pyrrolidinyl-benzamide Derivates", 1987, vol. 107, No. 9, pp. 711-719.
Japanese Office Action for 2019-548535 dated Dec. 8, 2020, with machine translation, 4 pages.
Korean Office Action for 10-2019-7018269, dated Feb. 1, 2021, with machine translation, 12 pages.
Chinese Office Action for 2020100794406, dated Nov. 16, 2020 with partial translation, 11 pages.
Ascalone V et Al: "Stereospecific determination of amisulpride, a new benzamide derivative, in human plasma and urine by automated solid-phase extraction and liquid chromatography on a chiral column Application to pharmacokinetics", Journal of Chromatography B, Elsevier Science Publishers, NL, vol. 676, No. 1, Feb. 9, 1996 (Feb. 9, 1996), pp. 95-105.
Marchese Giorgio et al: "Effect of the amisulpride isomers on rat catalepsy", European Journal of Pharmacology, vol. 444, No. 1-2, May 1, 2002 (May 1, 2002), pp. 69-74.
Grattan Vincent et al: "Antipsychotic Benzamides Amisulpride and LB-102 Display Polypharmacy as Racemates, S Enantiomers Engage Receptors D 2 and D 3 , while R Enantiomers Engage 5-HT 7", ACS OMEGA, vol. 4, No. 9, Aug. 15, 2019 (Aug. 15, 2019), pp. 14151-14154.
EP Search Report for EP Appl. No. 18801735.4, dated Mar. 1, 2021, 15 pages.
Office Action for Indonesian Patent Application No. PID201904405, dated Feb. 25, 2021, 3 pages (Unofficial English Translation).

* cited by examiner

PSYCHOTROPIC AGENTS AND USES THEREOF

PRIORITY CLAIM

This application is a continuation of application of U.S. application Ser. No. 16/383,933, filed Apr. 15, 2019 which is a continuation application of U.S. application Ser. No. 15/824,966, filed Nov. 28, 2017, now U.S. Pat. No. 10,259,786, issued Apr. 16, 2019, which claims the benefit of U.S. Provisional Application No. 62/427,062, filed Nov. 28, 2016, and U.S. Provisional Application No. 62/508,263, filed May 18, 2017, both of which are incorporated herein by reference in their entireties.

FIELD OF THE INVENTION

The present invention is generally in the field of pharmaceutical compositions and methods for the treatment of neuropsychiatric and/or psychological diseases or disorders.

BACKGROUND

Schizophrenia is a chronic debilitating mental illness affecting about one percent of the population. The disease manifests in delusional behavior, dysfunctional thinking, agitated body movement, social withdrawal, and depression. Schizophrenia patients suffer a profoundly reduced quality of life, and are ten times more likely to commit suicide that the general population.

Dopamine (particularly $D_2$ and $D_3$) antagonists are well recognized as improving symptoms of schizophrenia, and have been used clinically as such for decades. In the past twenty years it has become recognized that treatment of schizophrenia, as with many mental illnesses, benefits from engaging multiple receptors including serotonergic and adrenergic. Despite, literally, dozens of approved drugs to treat schizophrenia the disease remains poorly treated in many patients. Side effects of current medications include: dyskinesia, akathisia, weight gain, mood disturbances, sexual dysfunction, sedation, orthostatic hypotension, hypersalivation, and (in some cases) arganulocytosis.

Amisulpride (4-amino-N-(((1-ethyl-2-pyrrolidinyl)methyl)-5-(ethylsulfonyl))-2-methoxybenzamide) is an antipsychotic patented in 1981. Amisulpride binds selectively to the human dopaminergic $D_2$ ($K_i$ 2.8 nM) and $D_3$ ($K_i$ 3.2 nM) receptor subtypes without any affinity for $D_1$, $D_4$ and $D_5$ receptor subtypes. Unlike classical and atypical neuroleptics, amisulpride displays low affinity for serotonin, alpha-adrenergic, histamine receptor subtypes, muscarinic receptors and sigma sites though it has also been demonstrated to bind 5-$HT_{2B}$ and $HT_{7a}$ receptors with low double digit nM $K_i$. This ability of amisulpride to bind 5-HT receptors is thought to result in amisulpride's ability to treat symptoms of depression (sometimes noted in schizophrenia patients). Interestingly, compared to other antipsychotics, amisulpride is not noted to have any activity at the 5-$HT_{2a}$ receptor.

Despite the unique activities of amisulpride, amisulpride has low ability to cross blood brain barrier (BBB) to interact with the receptors in the brain. In a 2014 study, passive diffusion of amisulpride across a PAMPA membrane ($P_e$) was the lowest of 30 psychiatric drugs tested. Thus, dosing of amisulpride is high, typically 400 to 800 mg/d (though up to 1,200 mg/day is not uncommon). Such a high dose may cause adverse effects to the treated subjects.

SUMMARY OF THE INVENTION

Provided herein are novel amisulpride derivatives and pharmaceutical compositions thereof. In certain embodiments, the amisulpride derivatives disclosed herein are dopamine and/or serotonin antagonists. In certain embodiments, the amisulpride derivatives disclosed herein have improved membrane (e.g., BBB) permeability compared to amisulpride. In certain embodiments, the amisulpride derivatives can act as central nervous system (CNS) dopamine and/or serotonin antagonists. These amisulpride derivatives have structures of Formula I, Formula IA, Formula IB or Formula IC disclosed herein, including pharmaceutically acceptable salts thereof, and stereoisomers thereof (e.g., Formula I-S, Formula I-R, Formula IA-S, Formula IA-R, Formula IB-S, Formula IB-R, Formula IC-S, and Formula IC-R). Provided herein are also deuterated analogs of the amisulpride derivatives disclosed herein.

Also provided herein are methods for delivering a dopamine and/or serotonin (e.g., 5-HT2a) and/or alpha-2 adrenergic (α2) receptor antagonist to the brain of a subject comprising administering to the subject an amisulpride derivative disclosed herein or a pharmaceutical composition thereof; and the dopamine and/or serotonin and/or α2 receptor antagonist level in the brain is higher than administering to the subject amisulpride at a comparable dose.

Also provided herein are methods for antagonizing dopamine and/or serotonin (e.g., 5-HT2a) and/or α2 receptor in a subject comprising administering to a subject the amisulpride derivatives disclosed herein or pharmaceutical compositions thereof, either individually or in combination with other CNS active agents.

Also provided herein are methods for treating one or more conditions responsive to modulation of dopamine and/or serotonin (e.g., 5-HT2a) and/or α2 receptor in a subject comprising administering to a subject the amisulpride derivatives disclosed herein or pharmaceutical compositions thereof, either individually or in combination with other CNS active agents.

Also provided herein are methods for treating one or more disorders associated with an abnormality in levels of dopamine and/or serotonin in the brain, comprising administering to a subject the amisulpride derivatives disclosed herein or pharmaceutical compositions thereof, either individually or in combination with other CNS active agents.

Examples of the conditions responsive to modulation of dopamine and/or serotonin (e.g., 5-HT2a) and/or α2 receptor and/or and the disorders associated with abnormality in levels of dopamine and/or serotonin in the brain include, e.g., without limitation, mental illnesses. Examples of the mental illnesses include, without limitation, schizophrenia, symptoms of schizophrenia, schizoaffective disorder, bipolar disorder, depression, obsessive-compulsive disorder, Parkinson's psychosis, Alzheimer's psychosis, oppositional defiant disorder, aggression, suicidality, hostility, personality disorders, chronic fatigue syndrome, predominantly negative symptoms of schizophrenia, Charles Bonnet Syndrome, autism, and Tourette's disorder.

DETAILED DESCRIPTION OF THE INVENTION

Figure 1A:
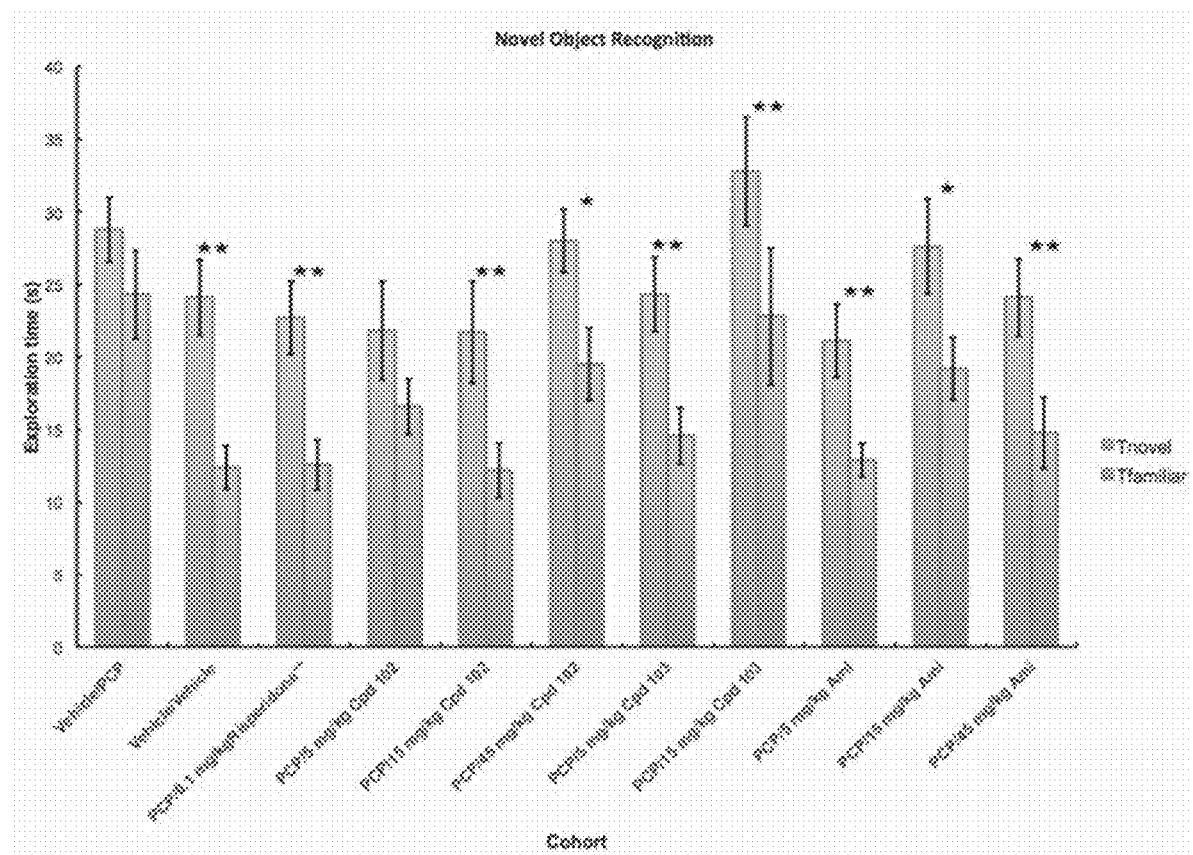
FIG. 1A: Novel object exploration data from a sub-chronic PCP NOR study in rats (±SEM, n=10/group). Differences in Discrimination index ((time spent exploring novel−time spent exploring familiar)/total exploration time) are depicted.

As disclosed herein, 4-amino substituted derivatives of amisulpride (also referred to as 4-amino amisulpride derivatives and 4-amino substituted amisulpride derivatives) showed improved membrane (e.g., BBB) permeability and may be used to target relevant receptors in the brain at a lower dose with less side effects to the treated subjects compared to amisulpride. For example, a 4-amino substituted amisulpride derivative Compound 102 (also referred to as LB-102, N-methyl amisulpride, and 4-methylamino substituted amisulpride derivative) was prepared (Examples 1 and 2) and showed unexpectedly high membrane permeability improvement compared to that of amisulpride (Example 4, 216.7 time improvement at pH 7.4, and 87.5 time improvement at pH 5). Stereoisomers of Compound 102 (Compound 103 and Compound 104) were also prepared (Example 3), as were other 4-amino amisulpride derivatives Compounds 105 to 110. Furthermore, the 4-amino substituted amisulpride derivatives showed effective binding to dopamine $D_2$ receptors and various CNS receptors (Examples 5-7). Unexpectedly, the 4-amino substituted amisulpride derivatives showed α2 (e.g., α2A, α2B, and α2C) receptor antagonism (Table 4, Example 7), while amisulpride displayed low affinity for α2 receptor. The 4-amino substituted amisulpride derivative showed 5-$HT_{2a}$ receptor antagonism (Table 4, Example 7), while amisulpride is not noted to have any activity at the 5-$HT_{2a}$ receptor. Furthermore, Compound 102 and Compound 103 were shown to restore known object exploration behavior in rats with impaired ability to discern between novel and familiar object in a Novel Object Recognition (NOR) assay (Example 8). The normalized amphetamine hyperactivities of Compounds 102 and 103 were statistically superior to or indistinguishable from that of amisulpride in an amphetamine-induced Locomotor Activity (LMA) assay (Example 9).

4-Amino Substituted Amisulpride Derivatives

Provided herein are amisulpride derivatives having a structure of Formula I:

Formula I

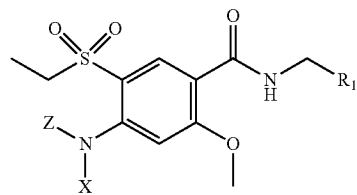

including pharmaceutically acceptable salts and stereoisomers thereof, wherein:
$R_1$ is

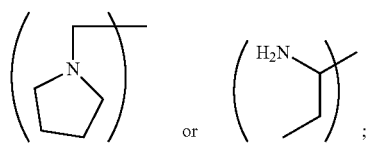

and

X and Z are the same or different and independently selected from the group consisting of hydrogen, alkyl (either branched or unbranched, such as methyl, ethyl, n-propyl, i-propyl, n-butyl, and s-butyl), alkenyl (either branched or unbranched, such as methyl, ethyl, n-propyl, i-propyl, n-butyl, and s-butyl), alkynyl (either branched or unbranched, such as methyl, ethyl, n-propyl, i-propyl, n-butyl, and s-butyl), cycloalkyl (e.g., cyclopropyl, cyclobutyl, cyclopentyl, and cyclohexyl), cycloalkylalkyl (e.g., cyclopropylmethyl, cyclobutylethyl, and cyclopentylethyl), heterocyclyl, heterocyclylalkyl, aryl (e.g., phenyl, naphthyl, tetrahydronapthyl, indanyl, and biphenyl), arylalkyl (e.g., —$CH_2C_6H_5$, and —$C_2H_5CH_5$), heteroarylalkyl (e.g., —$CH_2C_6H_4N$, and —$C_2H_5CH_4N$), and heteroaryl with one or two or three or more hetero ring atoms (such as pyridine, pyrrole, furan, thiophene, or pyrimidine), optionally the alkyl, alkenyl, alkynyl, cycloalkyl, cycloalkylalkyl, heterocyclyl, heterocyclylalkyl, aryl, arylalkyl, heteroarylalkyl, and heteroaryl groups are further substituted with one or more substitution groups selected from the group consisting of halogens such as chlorine, bromine and fluorine, amines, hydroxy groups, carboxylic acids, nitro groups, carbonyl and other alkyl and aryl groups as defined herein; with the proviso that at least one of X and Z is not hydrogen.

In certain embodiments, the amisulpride derivative is a stereoisomer having a structure of Formula I-S:

Formula I-S

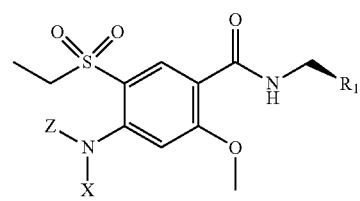

including pharmaceutically acceptable salts thereof, wherein Z, X, and $R_1$ are defined the same as above with respect to Formula I.

In certain embodiments, the amisulpride derivative is a stereoisomer having a structure of Formula I-R:

Formula I-R

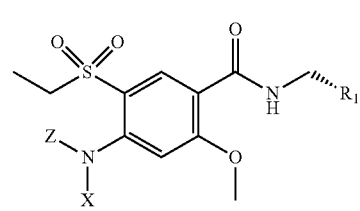

including pharmaceutically acceptable salts thereof, wherein Z, X, and $R_1$ are defined the same as above with respect to Formula I.

In certain embodiments, the amisulpride derivative is a 4-amino substituted derivative of amisulpride having a structure of Formula IA:

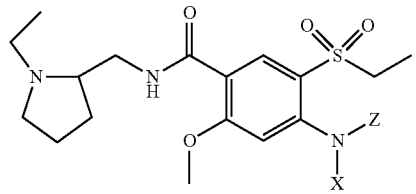

Formula IA including pharmaceutically acceptable salts and stereoisomers thereof, and X and are defined the same as above with respect to Formula I.

In certain embodiments, the 4-amino substituted derivative of amisulpride is a stereoisomer having a structure of Formula IA-S:

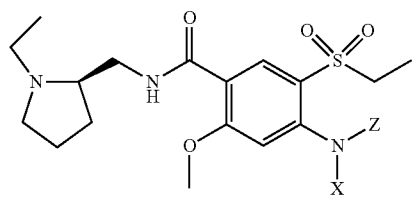

Formula IA-S including pharmaceutically acceptable salts thereof, and X and Z are defined the same as above with respect to Formula I.

In certain embodiments, the 4-amino substituted derivative of amisulpride is a stereoisomer having a structure of Formula IA-R:

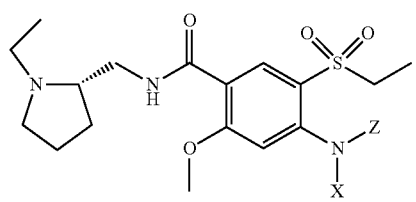

Formula IA-R including pharmaceutically acceptable salts thereof, and X and Z are defined the same as above with respect to Formula I.

In certain embodiments, the amisulpride derivative is a 4-amino substituted derivative of amisulpride having a structure of Formula IB:

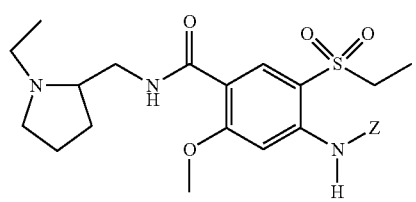

Formula IB including pharmaceutically acceptable salts and stereoisomers thereof, and Z is defined the same as above with respect to Formula I with the proviso that Z is not H.

In certain embodiments, the 4-amino substituted derivative of amisulpride is a stereoisomer having a structure of Formula IB-S:

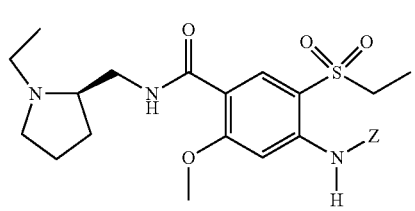

Formula IB-S including pharmaceutically acceptable salts thereof, and Z is defined the same as above with respect to Formula I with the proviso that Z is not H.

In certain embodiments, the 4-amino substituted derivative of amisulpride is a stereoisomer having a structure of Formula IB-R:

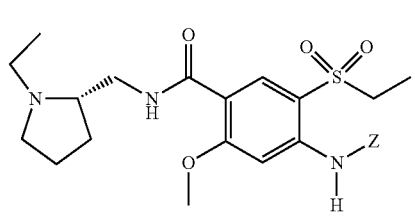

Formula IB-R including pharmaceutically acceptable salts thereof, and Z is defined the same as above with respect to Formula I with the proviso that Z is not H.

In certain embodiments, the amisulpride derivative has a structure of Formula IC:

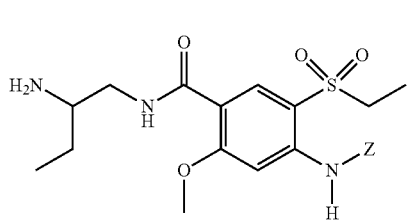

Formula IC including pharmaceutically acceptable salts and stereoisomers thereof, and Z is defined the same as above with respect to Formula I with the proviso that Z is not H.

In certain embodiments, the amisulpride derivative is a stereoisomer having a structure of Formula IC-S:

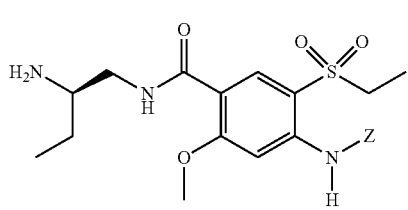

Formula IC-S including pharmaceutically acceptable salts thereof, and Z is defined the same as above with respect to Formula I with the proviso that Z is not H.

In certain embodiments, the amisulpride derivative is a stereoisomer having a structure of Formula IC-R:

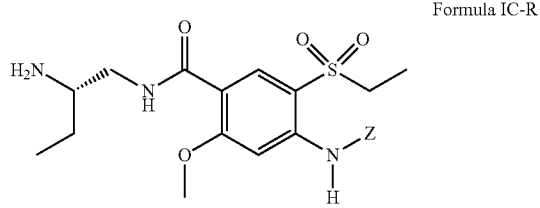

Formula IC-R including pharmaceutically acceptable salts thereof, and Z is defined the same as above with respect to Formula I with the proviso that Z is not H.

In certain embodiments, the amisulpride derivatives disclosed herein have greater membrane (e.g., BBB) permeability than amisulpride. In certain embodiments, the amisulpride derivatives disclosed herein are dopamine and/or serotonin and/or α2 antagonists. For example, the amisulpride derivatives disclosed herein bind to dopamine $D_2$ and/or $D_3$ receptors. In certain embodiments, the amisulpride derivatives disclosed herein more selectively bind to dopamine $D_2$ and/or $D_3$ receptor over dopamine $D_1$, $D_4$ and/or $D_5$ receptor. In certain embodiments, the amisulpride derivatives disclosed herein are capable of interacting dopamine and/or serotonin and/or α2receptors in CNS.

Provided herein are also deuterated analogs of the amisulpride derivatives disclosed herein, wherein one or more hydrogens of the amisulpride derivatives are replaced by deuterium. In certain embodiments, the one or more deuteriums in the deuterated analog are present in at least 100 times the natural abundance level.

Provided herein are pharmaceutical compositions comprising one or more of the amisulpride derivatives and deuterated analogs thereof disclosed herein and a pharmaceutically acceptable carrier. In certain embodiments, the one or more of the amisulpride derivatives the pharmaceutical compositions comprise are substantially enantiomerically pure, and such pharmaceutical compositions are also referred to as substantially enantiomerically pure pharmaceutical compositions. In certain embodiments, the term "substantially enantiomerically pure" means enantiomerical purity of about 50% or higher, about 60% or higher, about 70% or higher, about 80% or higher, about 90% or higher, about 95% or higher, or about 98% or higher.

Also provided herein are methods for delivering a dopamine and/or serotonin (e.g., 5-$HT_{2a}$) and/or α2 receptor antagonist to the brain of a subject comprising administering to the subject one or more of amisulpride derivatives and deuterated analogs thereof disclosed herein, or a pharmaceutical composition thereof; and the dopamine and/or serotonin (e.g., 5-$HT_{2a}$) and/or α2 receptor antagonist level in the brain is higher than administering to the subject amisulpride at a comparable dose. In certain embodiments, the amisulpride derivatives, deuterated analogs, and/or the pharmaceutical composition are substantially enantiomerically pure.

Also provided herein are methods for antagonizing dopamine and/or serotonin (e.g., 5-$HT_{2a}$) and/or α2 receptor in a subject comprising administering to a subject one or more of amisulpride derivatives and deuterated analogs thereof disclosed herein or a pharmaceutical composition thereof, either individually or in combination with other CNS active agents. In certain embodiments, the amisulpride derivatives, deuterated analogs, and/or the pharmaceutical composition are substantially enantiomerically pure.

Also provided herein are methods for treating one or more conditions responsive to modulation of dopamine and/or serotonin (e.g., 5-$HT_{2a}$) and/or α2 receptor in a subject comprising administering to a subject a therapeutically effective amount of one or more of amisulpride derivatives and deuterated analogs thereof disclosed herein or a pharmaceutical composition thereof, either individually or in combination with other CNS active agents. In certain embodiments, the amisulpride derivatives, deuterated analogs, and/or the pharmaceutical composition are substantially enantiomerically pure.

Provided herein are methods for treating one or more disorders associated with an abnormality in levels of dopamine and/or serotonin in the brain in a subject comprising administering to the subject a therapeutically effective amount of one or more of amisulpride derivatives and deuterated analogs thereof disclosed herein, or a pharmaceutical composition thereof. In certain embodiments, the amisulpride derivatives, deuterated analogs and/or the pharmaceutical composition are substantially enantiomerically pure.

In certain embodiments, the therapeutically effective amount of the amisulpride derivatives disclosed herein or the pharmaceutical composition thereof is lower than that of amisulpride. Accordingly, the methods disclosed herein may result in fewer adverse events to the subject treated.

Examples of conditions responsive to modulation of dopamine and/or serotonin (e.g., 5-$HT_{2a}$) and/or α2 receptor and/or disorders associated with an abnormality in levels of dopamine and/or serotonin in the brain include, e.g., without limitation, mental illnesses.

Examples of the mental illnesses include, without limitation, schizophrenia, symptoms of schizophrenia, schizoaffective disorder bipolar disorder, depression, obsessive-compulsive disorder, Parkinson's psychosis, Alzheimer's psychosis, oppositional defiant disorder, aggression, suicidality, hostility, personality disorders, autism, chronic fatigue syndrome, predominantly negative symptoms of schizophrenia, Charles Bonnet Syndrome, and Tourette's disorder.

As used herein, the singular for "a," "an," and "the" include plural references unless the context clearly dictates otherwise. For example, the term "a cell" includes a plurality of cells, including mixtures thereof. Similarly, use of "a compound" for treatment of preparation of medicaments as described herein contemplates using one or more compounds of the invention for such treatment or preparation unless the context clearly dictates otherwise.

As used herein, the term "comprising" is intended to mean that the compositions and methods include the recited elements, but not excluding others. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the composition of this invention. Embodiments defined by each of the transitional terms are within the scope of this invention.

The term "alkyl" refers to a straight or branched hydrocarbon chain radical consisting solely of carbon and hydrogen atoms, containing no unsaturation. Unless otherwise specified, the term "alkyl" refers to a group having one, two, three, four, five, six, seven, or eight carbon atoms (for example, one to six carbon atoms, or one to four carbon atoms), and which is attached to the rest of the molecule by a single bond. Examples of alkyl groups include, but are not limited to, methyl, ethyl, n-propyl, i-propyl, n-butyl, t-butyl, s-butyl, n-pentyl, and s-pentyl.

The term "alkenyl" refers to an aliphatic hydrocarbon group containing a carbon-carbon double bond and which may be a straight or branched or branched chain. Unless otherwise specified, the term "alkenyl" refers to a group having 2, 3, 4, 5, 6, 7, 8, 9, or 10 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbyl radical having at least one carbon-carbon triple bond. Unless otherwise specified, the term "alkynyl" refers to a group having in the range of 2, 3, 4, 5, 6, 7, 8, 9, 10, 11, or 12 carbon atoms (for instance, 2 to 10, 2 to 10 carbon atoms), e.g., ethynyl, propynyl, and butynyl.

The term "cycloalkyl" denotes a non-aromatic mono or multicyclic ring system of 3, 4, 5, 6, 7, 8, 9, 10, 11, or 12 carbon atoms such as cyclopropyl, cyclobutyl, cyclopentyl, and cyclohexyl.

The term "cycloalkylalkyl" refers to a cycloalkyl group as defined above directly bonded to an alkyl group as defined above.

The term "aryl" refers to a mono- or multi-cyclic aromatic radical having in the range of 6 up to 20 carbon atoms such as phenyl, naphthyl, tetrahydronapthyl, indanyl, and biphenyl.

The term "arylalkyl" refers to an aryl group as defined above directly bonded to an alkyl group as defined above, e.g., —$CH_2C_6H_5$, and —$C_2H_5CH_5$.

The term "heterocyclyl" refers to a non-aromatic 3 to 15 member ring radical which, consists of carbon atoms and at least one heteroatom selected from the group consisting of nitrogen, phosphorus, oxygen and sulfur. The heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized.

The term "heterocyclylalkyl" refers to a heterocyclyl group as defined above directly bonded to an alkyl group as defined above.

The term "heteroaryl" refers to an optionally substituted 5-14 member aromatic ring having one or more hetero ring atoms selected from the group consisting of N, O, and S as ring atoms. The heteroaryl may be a mono-, bi- or tricyclic ring system. Examples of such heteroaryl ring radicals includes, but are not limited to, oxazolyl, thiazolyl imidazolyl, pyrrolyl, furanyl, pyridinyl, pyrimidinyl, pyrazinyl, benzofuranyl, indolyl, benzothiazolyl, benzoxazolyl, carbazolyl, quinolyl and isoquinolyl.

The term "heteroarylalkyl" refers to an heteroaryl group as defined above directly bonded to an alkyl group as defined above, e.g., —$CH_2C_6H_4N$, and —$C_2H_5CH_4N$.

The term "subject" refers to a mammal, such as a domestic pet (for example, a dog or cat), or human. In certain embodiments, the subject is a human.

The phrase "effective amount" refers to the amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The term "pharmaceutically acceptable carrier" refers to a carrier that does not cause an allergic reaction or other untoward effect in patients to whom it is administered and are compatible with the other ingredients in the formulation. Pharmaceutically acceptable carriers include, for example, pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the therapeutic agent.

The term "salt" used herein is not limited as long as the salt is formed with a compound of the amisulpride derivatives and is pharmaceutically acceptable; preferred examples of salts include a hydrohalide salt (for instance, hydrochloride, hydrobromide, hydroiodide and the like), an inorganic acid salt (for instance, sulfate, nitrate, perchlorate, phosphate, carbonate, bicarbonate and the like), an organic carboxylate salt (for instance, acetate salt, maleate salt, tartrate salt, fumarate salt, citrate salt and the like), an organic sulfonate salt (for instance, methanesulfonate salt, ethanesulfonate salt, benzenesulfonate salt, toluenesulfonate salt, camphorsulfonate salt and the like), an amino acid salt (for instance, aspartate salt, glutamate salt and the like), a quaternary ammonium salt, and the like. In addition, hydrochloride salt, sulfate salt, methanesulfonate salt, acetate salt and the like are preferred as "pharmacologically acceptable salt" of the amisulpride derivatives disclosed herein.

Isomers of the amisulpride derivatives disclosed herein (e.g., geometric isomers, optical isomers, rotamers, tautomers, and the like) can be purified using general separation means, including for example recrystallization, optical resolution such as diastereomeric salt method, enzyme fractionation method, various chromatographies (for instance, thin layer chromatography, column chromatography, glass chromatography and the like) into a single isomer.

Pharmaceutical Formulations and Routes of Administration

The amisulpride derivatives disclosed herein and/or deuterated analogs thereof may be administered by a variety of routes including orally and by injection (e.g. subcutaneously, intravenously, and intraperitoneally). The amisulpride derivatives disclosed herein may be formulated into a pharmaceutical composition for use in the disclosed methods. Such compositions are prepared in accordance with acceptable pharmaceutical procedures such as described in Remington's Pharmaceutical Sciences, 17th edition, ed. Alfonso R. Gennaro, Mack Publishing Company, Eaton, Pa. (1985), which is incorporated herein by reference.

The amisulpride derivatives disclosed herein and/or deuterated analogs thereof may be administered orally in the form of a solid or liquid dosage form. In both, the amisulpride derivatives disclosed herein compound may be coated in a material to protect it from the action of acids and other natural conditions which may inactivate the compound. The amisulpride derivatives disclosed herein may be formulated as aqueous solutions, liquid dispersions, (ingestible) tablets, buccal tablets, troches, capsules, elixirs, suspensions, syrups, and wafers. The oral dosage forms may include excipients known in the art, such as binders, disintegrating agents, flavorants, antioxidants, and preservatives. Liquid dosage forms may include diluents such as saline or an aqueous buffer.

The amisulpride derivatives disclosed herein and/or deuterated analogs thereof may also be administered by injection. Formulations suitable for injection may include sterile aqueous solutions (where water soluble) or dispersions, and sterile powders for the extemporaneous preparation of sterile injectable solutions or dispersions. The pharmaceutical composition may be sterile and be fluid to the extent that easy syringability exists. It may be stable under the conditions of manufacture and storage and be preserved against the contaminating action of microorganisms such as bacteria and fungi. The pharmaceutically acceptable carrier can be a solvent or dispersion medium containing, for example, water, ethanol, polyol (such as, glycerol, propylene glycol, and liquid polyethylene glycol), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, and ascorbic acid. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the methods of preparation include vacuum drying and freeze-drying which yields a powder of the active ingredient (i.e., the therapeutic compound) plus any additional desired ingredient from a previously sterile-filtered solution thereof.

The actual dosage amount of the compound administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject.

In one embodiment, a human subject is administered the daily doses of from about 0.01 mg/kg to about 100 mg/kg.

Single or multiple doses of the compounds are contemplated. Desired time intervals for delivery of multiple doses can be determined by one of ordinary skill in the art employing no more than routine experimentation. As an example, subjects may be administered two doses daily at approximately 12 hour intervals. In some embodiments, the compound is administered once a day.

The amisulpride derivatives disclosed herein or pharmaceutical compositions thereof may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months. In other embodiments, the invention provides that the amisulpride derivatives disclosed herein or pharmaceutical compositions thereof agent(s) may be taken orally and that the timing of which is or is not dependent upon food intake. Thus, for example, the agent can be taken every morning and/or every evening, regardless of when the subject has eaten or will eat.

Combination Therapy

In addition to being used as a monotherapy, the amisulpride derivatives disclosed herein or pharmaceutical compositions thereof may also find use in combination therapies. Effective combination therapy may be achieved with a single pharmaceutical composition or pharmacological formulation that includes both agents, or with two distinct pharmaceutical compositions or pharmacological formulations, administered at the same time, wherein one composition includes a compound of this invention, and the other includes the second agent(s). Alternatively, the therapy may precede or follow the other agent treatment by intervals ranging from minutes to months.

The additional agent or agents may be selected from any agent or agents useful for treating a psychological disorder, for example any agent or agent and/or α2s useful for treating an imbalance of dopamine, serotonin, histamine, or glutamate. In one embodiment, the additional agent or agent is useful in improving psychological function, e.g., an antipsychotic, such as quetiapine, geodon, zyprexa, latuda, olanzapine, risperidone, iloperidone, ziprasidone, clozapine, haloperidol, chlorpromazine, citrlopram, escitalopram, paroxetine, fluoxetine, fluvoxamine, sertraline, desvenlafaxine, duloxetine, milnacipran, venlafaxine, vilazodone, and combinations thereof.

Synthesis of the Amisulpride Derivatives

The amisulpride derivatives disclosed herein of the present invention can be prepared from amisulpride (4-amino-N-((1-ethyl-2-pyrrolidinyl)methyl)-5-(ethylsulfonyl))-2-methoxybenzamide), which is readily available. The synthesis of amisulpride is described, for example, in U.S. Pat. No. 4,401,822.

The following synthesis for preparing the compounds of formula IB can be adapted to prepare other compounds of the present invention, such as compounds of Formulas I, IA and IC. The compound of formula IB can be prepared by (a) treating amisulpride with a mixture of a carboxylic acid and its corresponding anhydride to obtain the corresponding amide, (b) reduction of the amide to the amine with a suitable reducing agent, for example, borane:dimethyl sulfide to form a compound of Formula IB:

Formula IB

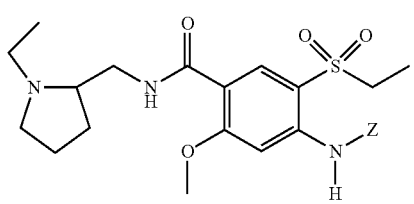

wherein Z is defined the same as above, and Z=—C—R. This reaction scheme is shown below:

Scheme 1.
Preparation of Amisulpride Derivatives

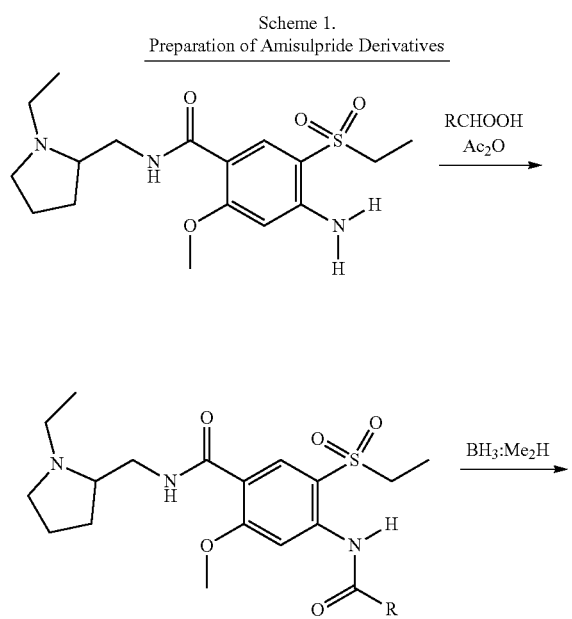

Similarly, compounds of Formula IA can be prepared by further substituting the N—H in the corresponding compound of Formula IB with the corresponding X group; and compounds of Formula IC can be prepared by acylation of the aniline nitrogen in the corresponding compound of Formula IB followed by reduction.

Additionally, 4-methylamino substituted amisulpride derivatives may be prepared by reacting amisulpride with N,N-dimethylformamide dimethyl acetal to provide the corresponding amide, which is then reduced by a reducing agent (e.g., $NaBH_4$, $DMS:BH_3$, Red-Al, and $LiAlH_4$) to provide the corresponding 4-methylamino substituted amisulpride derivatives.

Scheme 2.
Preparation of 4-Methylamino Substituted Amisulpride Derivatives

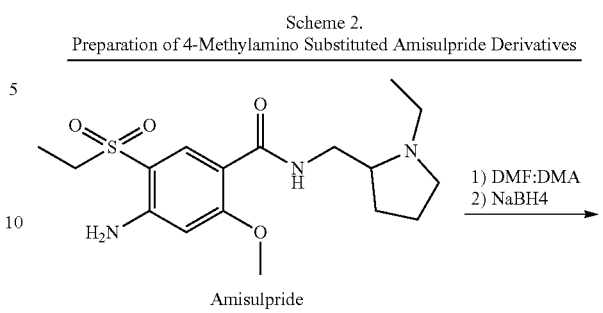

Stereoisomers of the amisulpride derivatives disclosed herein can be prepared similarly by using the corresponding stereoisomer of amisulpride as the starting material. For example, synthesis of ((S)-4-amino-N-((1-ethyl-2-pyrrolidinyl)methyl)-5-(ethylsulfonyl))-2-methoxybenzamide can be carried out as described in U.S. Pat. No. 6,169,094, which is incorporated herein by reference. The S isomers of the amisulpride derivatives can be prepared using the S isomer of amisulpride (Schemes 3 and 4). The R isomers of the amisulpride derivatives can be similarly prepared using the R isomer of amisulpride.

Scheme 3.
Preparation of Amisulpride Derivatives (S-Isomer as an example)

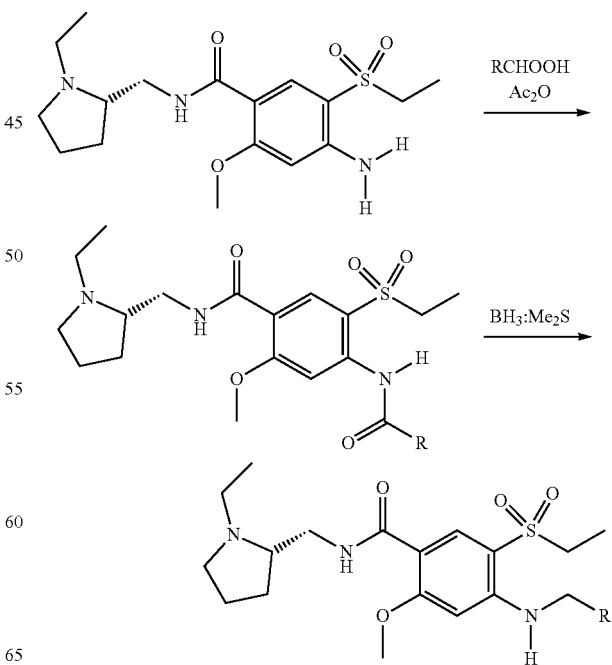

Scheme 4.
Preparation of 4-Methylamino Substituted Amisulpride Derivatives
(S-Isomer)

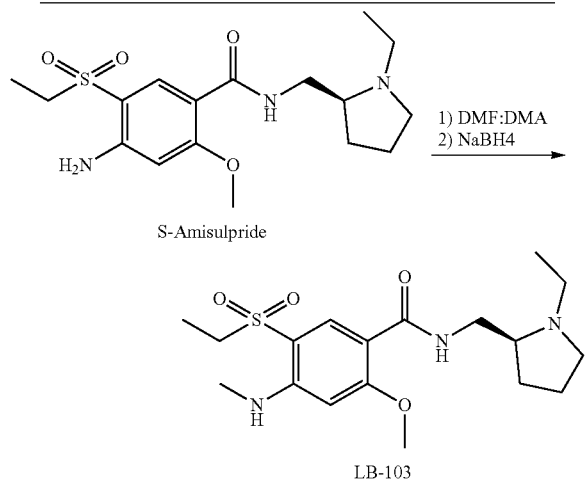

When neither Z or X of an amisulpride derivative of Formula I is hydrogen, the amisulpride derivative (di-substituted 4-amino amisulpride derivative) may be prepared by a two-step substitution of the 4-amino group. First, the 4-amino group is substituted with a first substitution group of Z or X as shown above to provide a mono-substituted 4-amino amisulpride derivative; and then the mono-substituted 4-amino amisulpride derivative is further substituted with a second substitution at the 4-amino to provide the desired di-substituted 4-amino amisulpride derivative. See, e.g., Examples 3C and 3D.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLES

Example 1: Synthesis of 4-formylamino-N-((1-ethyl-2-pyrrolidinyl)methyl)-5-(ethylsulfonyl))-2-methoxybenzamide (Compound 1)

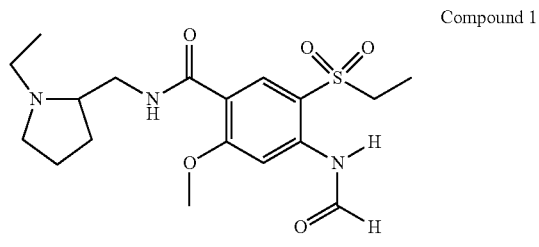 [SMILES: CCN1CCCC1CNC(=O)c1cc(S(=O)(=O)CC)c(NC=O)cc1OC]

Compound 1

To a solution of 4-amino-N-((1-ethyl-2-pyrrolidinyl)methyl)-5-(ethylsulfonyl))-2-methoxybenzamide (2 g, 5.5 mmol) in 20 mL formic acid, acetic anhydride (0.68 g, 6.6 mmol) was added portionwise at 5-10° C. The reaction mixture was stirred overnight at room temperature, and carefully poured into aq. K$_2$CO$_3$ at 5-10° C. Solid NaCl was added and the mixture was extracted with CHCl$_3$. The combined organic extracts were dried over Na$_2$SO$_4$, and the solvent evaporated under reduced pressure. The residue was purified by column chromatography on silica gel eluting with 5-10% MeOH in CHCl$_3$ to afford 1.82 g (83%) of a yellowish gum. $^1$H NMR (400 MHz, CDCl$_3$): δ 1.1 (t, 3H, CH$_3$), 1.3 (t, 3H, CH$_3$) 1.6 (br s, 2H), 1.7 (br s, 2H), 1.9 (br s, 1H), 2.3 (br s, 2H), 2.7 (br s, 1H), 2.9 (br s, 1H), 3.2 (q, 2H), 3.3 (br s, 1H), 3.4 (br s, 1H), 3.7 (m, 1H), 4.1 (s, 3H, OCH$_3$), 8.4 (br s, 1H, NH), 8.5 (s, 1H, H$_{ar}$), 8.6 (s, 1H, H$_{ar}$), 8.7 (s, 1H, CHO), 10.1 (s, 1H, NH). Expected Mol. Wt. [C$_{18}$H$_{27}$N$_3$O$_5$S]: 397.2, Observed Mol. Wt. 398.1 [M+H$^+$].

Example 2: Synthesis of 4-methylamino-N-((1-ethyl-2-pyrrolidinyl)methyl)-5-(ethylsulfonyl))-2-methoxybenzamide (Compound 102)

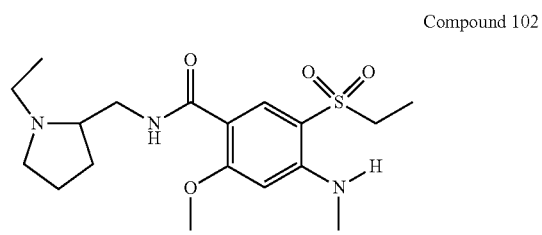 [SMILES: CCN1CCCC1CNC(=O)c1cc(S(=O)(=O)CC)c(NC)cc1OC]

Compound 102

To a solution of 4-formylamino-N-((1-ethyl-2-pyrrolidinyl)methyl)-5-(ethylsulfonyl))-2-methoxybenzamide (Compound 1, 1.82 g, 4.6 mmol) in 80 mL THF, BH$_3$Me$_2$S (1.09 mL, 11.5 mmol) was added portionwise at 5-10° C. The reaction mixture was stirred at 60° C. for 3 h, and carefully quenched with MeOH (40 mL). The reaction mixture was acidified with 10% HCl (15 mL) and the mixture was stirred at 60° C. overnight. The solvents were evaporated under reduced pressure, the aqueous residue was diluted with H$_2$O and basified with aq NaOH to pH 10. The mixture was extracted with CHCl$_3$, the combined organic extracts were dried over Na$_2$SO$_4$ and evaporated. The residue was purified by column chromatography on silica gel eluting with 5-10% MeOH in CHCl$_3$, following by purification by RP-HPLC eluting with a gradient MeCN-H$_2$O+0.1% TFA. The fractions containing the target material were partially evaporated under reduced pressure, basified with aq NaOH to pH 10, and extracted with CH$_2$Cl$_2$. The combined extracts were dried with Na$_2$SO$_4$ and evaporated under reduced pressure to afford the product as a white solid after standing which solidified upon storage (0.93 g, 53%). $^1$H NMR (400 MHz, CDCl$_3$): δ 1.1 (t, 3H, CH$_3$), 1.3 (t, 3H, CH$_3$), 1.6 (m, 3H), 1.9 (m, 1H), 2.2 (m, 2H), 2.5 (m, 1H), 2.7 (m, 1H), 2.9 (app d, 3H, NHCH$_3$), 3.1 (q, 2H, CH$_2$), 3.2 (m, 1H), 3.3 (m, 1H), 3.6 (m, 1H), 4.0 (s, 3H, OCH$_3$), 6.1 (s, 1H, Ha), 6.8 (br s, 1H, Ha), 8.1 (br s, NH), 8.5 (s, 1H, NH). $^{13}$C NMR (75 MHz, CDCl$_3$): δ 8.2, 14.9, 21.2, 29.0, 29.9, 40.5, 47.8, 49.5, 53.7, 56.9, 61.0, 92.1, 110.2, 111.9, 136.1, 150.0, 162.2, 164.0. Expected Mol. Wt. [C$_{18}$H$_{29}$N$_3$O$_4$S]: 383.2, Observed Mol. Wt. 384.5 [M+H$^+$].

Example 3: Synthesis of Stereoisomers (Compounds 103 and 104) of Compound 102, and 4-amino amisulpride derivatives (Compounds 105 to 110)

A): Synthesis of ((S)-4-methylamino-N-((1-ethyl-2-pyrrolidinyl)methyl)-5-(ethylsulfonyl))-2-methoxybenzamide (Compound 103)

((S)-4-amino-N-((1-ethyl-2-pyrrolidinyl)methyl)-5-(ethylsulfonyl))-2-methoxybenzamide (11.1 g) was suspended in N,N-dimethylformamide dimethyl acetal (33 mL) and stirred for 2 hours at 90° C. The reaction mixture was cooled to room temperature and $NaBH_4$ (4 g) was added portionwise. The mixture was stirred at room temperature for 1 h. Saturated $NaCHO_3$ (50 mL) was added to quench the reaction, and the resulting suspension was extracted with dichloromethane (2×50 mL). The organic phase was washed with brine, dried, filtered, and the solvent removed under reduced pressure. The residue was purified by column chromatography, eluting with $CH_2Cl_2$/MeOH/$NH_3$, to afford the product as a white solid that was further purified by recrystallization from acetone (5.3 g).

$^1$H NMR (400 MHz, DMSO-$d_6$): δ 1.1 (2t, 2X3H, $CH_3$), 1.5 (2, 1H) 1.6 (m, 2H), 1.8 (m, 1H), 2.1 (m, 1H), 2.3 (m, 2H), 2.5 (t, 1H), 2.6 (m, 1H), 2.7 (m, 1H), 2.9 (t, 3H), 3.1 (3, 2H), 3.2 (m, 2H), 3.3 (m, 3H), 3.5 (m, 1H), 4.0 (s, 3H, $OCH_3$), 6.3 (s, 1H$_{ar}$), 6.6 (m, 1H$_{ar}$), 8.1 (m, 1H, NH), 8.3 (s, 1H, NH). $^{13}$C NMR (100 MHz, DMSO-$d_6$): δ 7.56, 14.51, 23.05, 28.54, 30.39, 41.64, 47.90, 48.77, 53.62, 56.79, 62.36, 94.45, 109.94, 111.63, 135.68, 151.48, 163.14, 163.82. Expected Mol. Wt. [$C_{18}H_{27}N_3O_4S$] 383.2, Observed Mol. Wt. 384.4 [M+H$^+$].

B): Synthesis of ((R)-4-methylamino-N-((1-ethyl-2-pyrrolidinyl)methyl)-5-(ethylsulfonyl))-2-methoxybenzamide (Compound 104)

((S)-4-amino-N-((1-ethyl-2-pyrrolidinyl)methyl)-5-(ethylsulfonyl))-2-methoxybenzamide (11.2 g) was suspended in N,N-dimethylformamide dimethyl acetal (33 mL) and stirred for 2 hours at 90° C. The temperature was reduced to 70° C. and $NaBH_4$ (4 g) was added in 1 g portions at intervals of 20 minutes. After completion of the addition, the reaction mixture was left to stir a further hour at 90° C. The reaction mixture was cooled in an ice bath and the reaction quenched by addition of 150 mL of saturated $NaHCO_3$. The resulting solution was extracted with $CH_2Cl_2$ (5×50 mL) and the combined organic extracts dried over $Na_2SO_4$. Purification was achieved by column chromatography, eluting with 10% MeOH/$CH_2Cl_2$ to afford 7.9 g of a white solid.

$^1$H NMR (300 MHz, CDCl$_3$): δ 1.2 (t, 3H, $CH_3$), 1.3 (t, 3H, $CH_3$), 1.7 (m, 1H) 1.8 (m, 2H), 1.9 (m, 1H), 2.3 (m, 2H), 2.7 (m, 1H), 2.9 (m, 1H), 2.9 (d, 1H), 3.1 (q, 2H), 3.3 (m, 2H), 3.7 (m, 1H), 4.0 (s, 3H, $OCH_3$), 6.1 (s, 1H$_{ar}$), 6.8 (m, 1H$_{ar}$), 8.1 (m, 1H, NH), 8.6 (s, 1H, NH). Expected Mol. Wt. [$C_{18}H_{27}N_3O_4S$] 383.2, Observed Mol. Wt. 384.2 [M+H$^+$].

C): Synthesis of (4-dimethylamino-N-((1-ethyl-2-pyrrolidinyl)methyl)-5-(ethylsulfonyl))-2-methoxybenzamide (Compound 105)

4-methylamino-N-((1-ethyl-2-pyrrolidinyl)methyl)-5-(ethylsulfonyl))-2-methoxybenzamide (500 mg) was stirred in 10 mL formic acid at 30° C. for 21 h as $NaBH_4$ (8 equiv) was added in two portions and washed with aqueous NaOH to afford 408 mg of compound 105.

$^1$H NMR (400 MHz, CDCl$_3$): δ 1.2 (t, 3H, $CH_3$s), 1.7 (m, 1H), 1.8 (m, 2H), 1.9 (m, 1H), 2.2 (m, 2H), 2.7 (m, 1H), 3.2 (m, 1H), 3.3 (m, 1H), 3.4 (q, 2H), 4.0 (s, 3H, $OCH_3$), 6.8 (s, 1H$_{ar}$), 8.0 (s, 1H, NH) 8.8 (s, 1H). $^{13}$C NMR (100 MHz, CDCl$_3$): δ 7.38, 14.21, 22.96, 28.40, 41.24, 46.14, 48.39, 53.66, 56.11, 62.19, 104.94, 118.52, 126.17, 136.07, 157.93, 161.56, 163.79. Expected Mol. Wt. [$C_{19}H_{31}N_3O_4S$] 397.2, Observed Mol. Wt. 398.2 [M+H$^+$].

D): Synthesis of (4-ethylmethylamino-N-((1-ethyl-2-pyrrolidinyl)methyl)-5-(ethylsulfonyl))-2-methoxybenzamide (Compound 106)

4-methylamino-N-((1-ethyl-2-pyrrolidinyl)methyl)-5-(ethylsulfonyl))-2-methoxybenzamide (500 mg) was stirred in 6 mL 1,2-dichlororethane and sodium triacetoxyborohydride (1 g) and acetaldehyde (219 uL) were added and stirred at room temperature for 17 hours. The reaction was quenched by addition of aqueous NaOH and the product extracted into dichloromethane and purified by column chromatography to afford 98 mg of compound 106.

$^1$H NMR (400 MHz, CDCl$_3$): δ 1.2 (m, 6H, 2 $CH_3$s), 1.6 (m, 1H), 1.7 (m, 2H), 1.9 (m, 1H), 2.2 (m, 2H), 2.6 (m, 1H), 2.9 (m, 1H), 3.1 (q, 1H), 3.3 (m, 2H), 3.5 (q, 1H), 3.8 (m, 1H) 4.0 (s, 3H, $OCH_3$), 6.8 (s, 1H$_{ar}$), 8.0 (s, 1H, NH) 8.8 (s, 1H). $^{13}$C NMR (100 MHz, CDCl$_3$): δ 7.36, 12.84, 23.00, 28.42, 41.27, 42.99, 48.12, 52.30, 53.70, 56.16. 106.05, 126.41, 130.05, 142.41, 157.554, 157.54, 161.48, 163.90. Expected Mol. Wt. [$C_{20}H_{33}N_3O_4S$] 411.3, Observed Mol. Wt. 412.3 [M+H$^+$].

E): Synthesis of (4-ethylamino-N-((1-ethyl-2-pyrrolidinyl)methyl)-5-(ethylsulfonyl))-2-methoxybenzamide (Compound 107)

(Ethyl-2-pyrrolidinyl)methyl)-5-(ethylsulfonyl))-2-methoxybenzamide (500 mg) was stirred in 6 mL 1,2-dichloroethane with 0.4 mL acetic acid. The mixture was cooled on an ice bath and 1.15 g sodium triacetoxyborohydride was added. The mixture was stirred at room temperature overnight. The reaction was quenched by addition of aqueous NaOH and the product extracted into dichloromethane and purified by column chromatography and recrystallized from acetone/MTBE to afford 309 mg of compound 107.

$^1$H NMR (400 MHz, CDCl$_3$): δ 1.1 (br t, 3H, $CH_3$), 1.3 (t, 3H, $CH_3$), 1.4 (t, 3H, $CH_3$), 1.5-1.8 (m, 5H), 1.8 (m, 1H), 2.2 (m, 2H), 2.7 (m, 1H), 2.9 (m, 1H), 3.1 (q, 2H), 3.3 (m 2H), 3.7 (m, 1H), 4.0 (s, 3H, $OCH_3$), 6.1 (s, 1H$_{ar}$), 6.7 (s, 1H$_{ar}$), 8.1 (s, 1H, NH) 8.6 (s, 1H). $^{13}$C NMR (100 MHz, CDCl$_3$): δ 7.34, 14.17, 22.96, 28.47, 37.99, 41.35, 48.00, 49.82, 53.70, 55.80, 62.38, 93.35, 110.89, 111.91, 136.76, 150.76, 162.90, 164.29. Expected Mol. Wt. [$C_{19}H_{31}N_3O_4S$] 397.2, Observed Mol. Wt. 398.2 [M+H$^+$].

F): Synthesis of (4-isopropylamino-N-((1-ethyl-2-pyrrolidinyl)methyl)-5-(ethylsulfonyl))-2-methoxybenzamide (Compound 108)

(Ethyl-2-pyrrolidinyl)methyl)-5-(ethylsulfonyl))-2-methoxybenzamide (500 mg) was stirred in 6 mL DMF with 0.12 mL acetone. The mixture was cooled on an ice bath and 0.3 mL TFA was added followed by addition of 441 mg sodium triacetoxyborohydride. The mixture was stirred at 40° C. overnight. The reaction mixture was poured into aqueous NaOH and the product extracted into dichloromethane and purified by column chromatography to afford 550 mg of compound 108.

$^1$H NMR (400 MHz, CDCl$_3$): δ 1.1 (br t, 3H, CH$_3$), 1.2 (t, 3H, CH$_3$), 1.3 (t, 6H, CH$_3$), 1.6 (m, 2H), 1.7 (m, 2H), 1.9 (m, 1H), 2.2 (m, 1H), 2.6 (m, 1H), 2.9 (m, 1H), 2.1 (q, 2H), 3.2 (m, 2H), 3.7 (m, 1H), 4.0 (s, 3H, OCH$_3$), 6.1 (s, 1H$_{ar}$), 6.7 (s, 1H$_{ar}$), 8.0 (s, 1H, NH) 8.6 (s, 1H). $^{13}$C NMR (100 MHz, CDCl$_3$): δ 7.36, 22.45, 23.02, 28.48, 41.35, 44.15, 49.95, 53.74, 55.80, 93.65, 111.83, 136.69, 150.03, 162.87, 164.33. Expected Mol. Wt. [C$_{20}$H$_{33}$N$_3$O$_4$S] 411.2, Observed Mol. Wt. 412.2 [M+H$^+$].

G): Synthesis of (4-n-propylamino-N-((1-ethyl-2-pyrrolidinyl)methyl)-5-(ethylsulfonyl))-2-methoxybenzamide (Compound 109)

(Ethyl-2-pyrrolidinyl)methyl)-5-(ethylsulfonyl))-2-methoxybenzamide (500 mg) was stirred in 6 mL 1,2-dichloroethane with 0.3 mL proprionaldehyde. Sodium triacetoxyborohydride (1.2 g) was added in two portions 10 minutes apart, and the mixture was left to stir overnight. The reaction mixture was poured into aqueous NaOH and the product extracted into ethyl acetate and purified by column chromatography to afford 518 mg of compound 109.

$^1$H NMR (400 MHz, CDCl$_3$): δ 1.1 (br t, 3H, CH$_3$), 1.2 (t, 3H, CH$_3$), 1.3 (t, 6H, CH$_3$), 1.6 (m, 2H), 1.7 (m, 2H), 1.9 (m, 1H), 2.2 (m, 1H), 2.6 (m, 1H), 2.9 (m, 1H), 2.1 (q, 2H), 3.2 (m, 2H), 3.7 (m, 1H), 4.0 (s, 3H, OCH$_3$), 6.1 (s, 1H$_{ar}$), 6.7 (s, 1H$_{ar}$), 8.0 (s, 1H, NH) 8.6 (s, 1H). $^{13}$C NMR (100 MHz, CDCl$_3$): δ 7.36, 22.45, 23.02, 28.48, 41.35, 44.15, 49.95, 53.74, 55.80, 93.65, 111.83, 136.69, 150.03, 162.87, 164.33. Expected Mol. Wt. [C$_{20}$H$_{33}$N$_3$O$_4$S] 411.2, Observed Mol. Wt. 412.2 [M+H$^+$].

H): Synthesis of (4-benzylamino-N-((1-ethyl-2-pyrrolidinyl)methyl)-5-(ethylsulfonyl))-2-methoxybenzamide (Compound 110)

(Ethyl-2-pyrrolidinyl)methyl)-5-(ethylsulfonyl))-2-methoxybenzamide (500 mg) was stirred in 7 mL DMF with 1.25 mL benzaldehyde and 1 mL TFA. Sodium triacetoxyborohydride (3.5 g) was added in two portions, and the mixture was left to stir overnight at 40° C. The reaction mixture was poured into aqueous NaOH and the product extracted into dichloromethane and purified by column chromatography to afford 366 mg of compound 110.

$^1$H NMR (400 MHz, CDCl$_3$): δ 1.2 (t, 3H, CH$_3$), 1.2-1.3 (3, 3H), 1.5-1.8 (m, 3H), 1.8-2.0 (m, 1H), 2.3 (m, 2H), 2.6 (br s, 1H), 2.9 (m, 1H), 3.1-3.3 (m, 1H), 3.7 (m, 1H), 3.8 (s, 3H), 4.5 (br s, 2H), 3.7 (m, 1H), 4.0 (s, 3H, OCH$_3$), 6.1 (s, 1H$_{ar}$), 7.4 (m, 5H), 8.0 (s, 1H, NH) 8.6 (s, 1H). $^{13}$C NMR (100 MHz, CDCl$_3$): δ 7.36, 14.20, 22.91, 28.5, 41.32, 47.52, 50.03, 53.65, 55.77, 62.32, 94.62, 111.36, 112.24, 126.95, 128.97, 136.59, 137.43, 150.53, 162.69, 1664.15. Expected Mol. Wt. [C$_{24}$H$_{33}$N$_3$O$_4$S] 459.2, Observed Mol. Wt. 460.2 [M+H$^+$].

Example 4: Membrane Permeability of Compound 102

Membrane permeability of 4-methylamino-N-((1-ethyl-2-pyrrolidinyl)methyl)-5-(ethylsulfonyl))-2-methoxybenzamide) (Compound 102) was measured using a PAMPA assay at pH 5 and 7.4. Specifically, 10 mM solutions of controls ranitidine (3.5 mg in 1 mL DMSO) and propanolol (2.9 mg in 1 mL DMSO), N-methyl amisulpride (3.3 mg in 0.8 mL DMSO), and amisulpride (3.4 mg in 0.9 mL DMSO) were prepared. Diffusion across a Pion PAMPA membrane were measured at pH 5 and pH 7.4, as shown in Table 1, respectively

TABLE 1

Permeability of Compound 102, amisulpride, propanolol, and ranitidine through a PAMPA membrane at pH 5 and 7.4.

| Test Compound | Permeability (cm/s) pH 5 | Permeability (cm/s) pH 7.4 |
|---|---|---|
| Amisulpride | 2.4 × 10$^{-10}$ | 2.4 × 10$^{-11}$ |
| N-methyl amisulpride (Compound 102) | 2.1 × 10$^{-8}$ | 5.2 × 10$^{-9}$ |
| Promanolol | 3.1 × 10$^{-8}$ | 7.8 × 10$^{-6}$ |
| Ranitidine | 1.1 × 10$^{-10}$ | 1.5 × 10$^{-10}$ |

Example 5: Binding of Compound 102 to Dopamine D$_2$ Receptors (Cell-Based Assay)

The ability of Compound 102 to bind dopamine D$_2$ receptors was measured in a cell-based assay. Dopamine D$_2$ receptor cells were seeded in a half a black, clear-bottomed 96 well plate. At a density of 15,000 cells/well to a volume of 25 μL and were left to incubate overnight. Calcium 5 dye in HEPES buffered HBSS (Hanks' balanced salt solution) was prepared and 10 μL was added to each well and the mixture was left to sit at 37° C. for 1 hour. After equilibration, 5 μL of the test compound and controls were added to the wells and incubated at room temperature for 10 minutes. Fluorescence was measured every 1.52 seconds. After 20 seconds 10 μL of dopamine (at EC$_{80}$ concentration) was added and the fluorescence monitored for 2 minutes with excitation at 452 nm and emission at 525 nm. Cell-based IC$_{50}$ values for Compound 102, together with known dopamine D$_2$ inhibitors risperidone, amisulpride, and clozapine are presented in Table 2.

TABLE 2

IC$_{50}$ values for Compound 102, risperidone, amisulpride, and clozapine against dopamine D2 receptors (cell-based assay).

| Compound | D$_2$ IC$_{50}$ nM |
|---|---|
| Compound 102 | 8.9 |
| Risperidone | 3.6 |
| Amisulpride | 1.5 |
| Clozapine | 7100 |

Example 6: Binding of Compound 102 to Dopamine D$_2$ Receptors (Membrane Preparation)

The ability of Compound 102 to bind the dopamine D$_2$ receptor in a membrane preparation was examined. Medium was removed from dopamine D$_2$ receptor cells and washed with PBS. A lysis buffer (250 mM sucrose, 1 nM EDTA, 10 mM Tris HCl buffered at pH 7.2 plus protease inhibitors) was added and cells scrapped using a plate scrapper. Cells were homogenized with 20 manual up and down strokes in a glass homogenizer. Intact cells, nuclei, and cell debris were removed by centrifugation of the homogenate at 500×g for 10 minutes at 4° C., the supernatant was removed, and the pellet resuspended in assay buffer.

Membrane preparations were incubated with $^3$H spiperone until equilibration. Separation of bound from free radioligand was carried out using a Packard Filtermate Harvester and glass filter plates. Radioactivity was measured using a Packard Topcount. To 20 μL of D2 membranes were mixed 20 μL of $^3$H spiperone and 10 μL test compound or reference ligand in binding buffer in a nonbinding 96 well plate, and incubated for <120 minutes. Prior to filtration, a 96 well harvest filter plate was coated with 0.33% polyethyleneimine for 30 minutes and then washed with assay buffer. The binding reaction was transferred to the filter plate and washed three times with wash buffer, dried, scintillant added, and radioactivity counted on a Topcount NXT.

Compound 102, risperidone, amisulpride, and clozapine were tested using 0.1 nM $^3$H spiperone at concentrations of 1000, 100, 10, 1, 0.1, and 0.01 nM in triplicate. $IC_{50}$ values for this membrane based assay are presented in Table 3.

TABLE 3

$IC_{50}$ values for Compound 102, risperidone, amisulpride, and clozapine against dopamine D2 receptors (membrane based assay).

| Compound | $D_2$ $IC_{50}$ nM |
|---|---|
| Compound 102 | 8.2 |
| Risperidone | 10.4 |
| Amisulpride | 8.5 |
| Clozapine | 2800 |

Example 7: Binding of Compound 102 and Compound 103 to Various CNS Receptors (Dopamine $D_2$. Dopamine $D_3$. A 2 Adrenergic, and 5-$HT_{2a}$ Receptors) (Table 4)

The ability of Compound 102 and 103 to bind $\alpha_2$ (non-selective), $\alpha_{2A}$, $\alpha_{2B}$, $\alpha_{2C}$, 5-$HT_{2A}$ (agonist), 5-$HT_{2A}$ (antagonist), $D_{2L}$, $D_{2S}$, and $D_3$ was measured at concentrations ranging from $10 \times 10^{-5}$ to $10 \times 10^{-9}$ M and measuring displacement of reference ligands (prazosin for $\alpha_2$ (non-selective), yohimbine for $\alpha_{2A}$, $\alpha_{2B}$ and $\alpha_{2C}$, DOI ([2,5-dimethoxy-4-iodophenyl]-2-aminopropane) for 5-$HT_{2A}$ (agonist), ketanserine for 5-$HT_{2A}$ (antagonist), butaclamol for $D_{2L}$, 7-OH-DPAT for $D_{2S}$, and (+) blutaclamol for $D_3$). bound to the respective isolated receptor. Inhibition data are reported in Table 4.

TABLE 4

$IC_{50}$ and Ki values for Compounds 102 (LB102) and Compound 103 (LB103) against various CNS receptors in a cell based assay.

| | IC50 (nM) | | Ki (nM) | |
|---|---|---|---|---|
| | LB102 | LB103 | LB102 | LB103 |
| $\alpha^*_{2A}$ (non-selective) | 95 | 150 | 41 | 6.7 |
| $\alpha^*_{2A}$(h) | 480 | | 220 | |
| $\alpha^*_{2B}$(h) | 170 | | 110 | |
| $\alpha^*_{2C}$(h) | 790 | | 240 | |
| 5-$HT_{2a}$ (agonist) | 270 | 550 | 200 | 410 |
| 5-$HT_{2a}$ (antagonist) | 890 | 980 | 490 | 530 |
| 5-$HT_\gamma$ | 74 | | 27 | |
| D2L | 2.7 | 1.7 | 0.66 | 0.41 |
| D2S | 8.4 | 1.4 | 3.4 | 0.56 |
| D3 | 11 | 5.5 | 2.5 | 1.2 |

Example 8: Novel Object Recognition (NOR) Assay Showed Efficacies of Compounds 102 and 103

Efficacy of Compounds 102 and 103 was evaluated in rats in a Novel Object Recognition (NOR) assay, a well-established model recapitulating cognitive and negative aspects of the PANSS scale of schizophrenia. In this assay, animals were treated for several weeks with a low dose of phencyclidine (PCP) to impair the ability of the rat to discern between novel and familiar objects. Typically rats, like humans, would spend more time exploring a novel object than a familiar one. The efficacy in this study was demonstrated by the ability of the test treatment to restore normal brain function as manifested by reversing the PCP impairment.

Figure 1B:
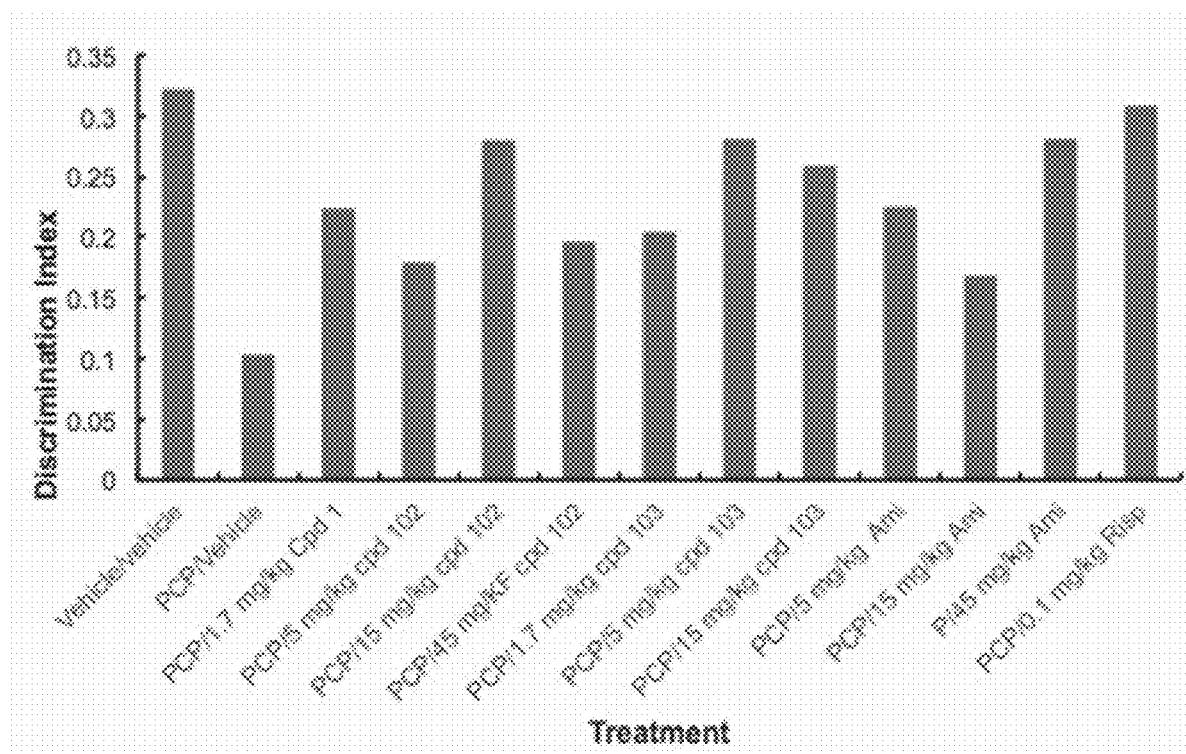
FIG. 1B: Discrimination index data from a sub-chronic PCR NOR study in rats (n=10/group). Differences in discrimination index ((time spent exploring novel−time spent exploring familiar)/total exploration time) are depicted.

In this NOR study the efficacy of Compounds 102 and 103 was compared to known antipsychotics amisulpride and risperidone for its ability to restore normal differentiation between novel and familiar object exploration in PCP-treated rats. Rats (n=10/group) were dosed with 2 mg/kg intraperitoneal twice a day (i.p., b.i.d.) for seven days followed by 7 days drug free. Cognitive measurements, at various PO doses test agent, were taken at 3 hours post-dose for Compound 102, 103, and amisulpride and at 30 minutes for risperidone. Novel object exploration time was measured for the test subjects from a sub-chronic PCP NOR study in rats (n=10/group). The differences in exploration time between novel (Tnovel¬) and familiar (Tfamliar) objects are depicted in FIG. 1A (*: p<0.05; and **: p<0.01). FIG. 1B shows discrimination index of the NOR study obtained by the following Equation 1:

$$\text{Discrimination index} = (\text{time spent exploring novel} - \text{time spent exploring familiar})/\text{total exploration time} \quad \text{(Equation 1)}$$

FIGS. 1A and 1B show that all doses of Compounds 102 and 103, save one, increased the difference between novel and familiar object exploration time in a manner consistent with currently used antipsychotics amisulpride and risperidone.

In the NOR study depicted in FIGS. 1A and 1B, Compounds 102 and 103 were able to restore known object exploration behavior in rats treated with PCP to levels similar to untreated rats, and on par with values obtained using known antipsychotics Amisulpride and Risperidone.

Example 9: Amphetamine-Induced Locomotor Activity (LMA) Assay Showed Efficacies of Compounds 102 and 103

Efficacy of Compounds 102 and 103 was studied in rats in an amphetamine-induced Locomotor Activity (LMA) assay, a measure of positive aspects of the PANSS scale. In the LMA assay rats were dosed with amphetamine (Amp, 1 mg/kg, s.c.), causing excessive movement, in a cage with sensors that monitored how far each rat moved. Rats dosed with amphetamine alone tended to show hypermobility while rats dosed with antipsychotics showed more normal, calmer, activity.

In this LMA study Compounds 102 (Cpd 102, 30 mg/kg) and 103 (Cpd 103, 30 mg/kg), amisulpride (30 mg/kg), and risperidone (1 mg/kg) were dosed orally in groups of 10 rats. Distance moved, over the course of an hour, was measured 6 hours post dosing for Compounds 102 and 103 and amisulpride-risperidone was dosed 1 hour prior to measurement. The endpoint of this study was total ambulatory distance (the distance traveled by each animal in the cage). Total ambulatory distance data from this amphetamine induced LMA study are summarized in FIG. 2 (*:p<0.01; **: p<0.05).

Figure 2:
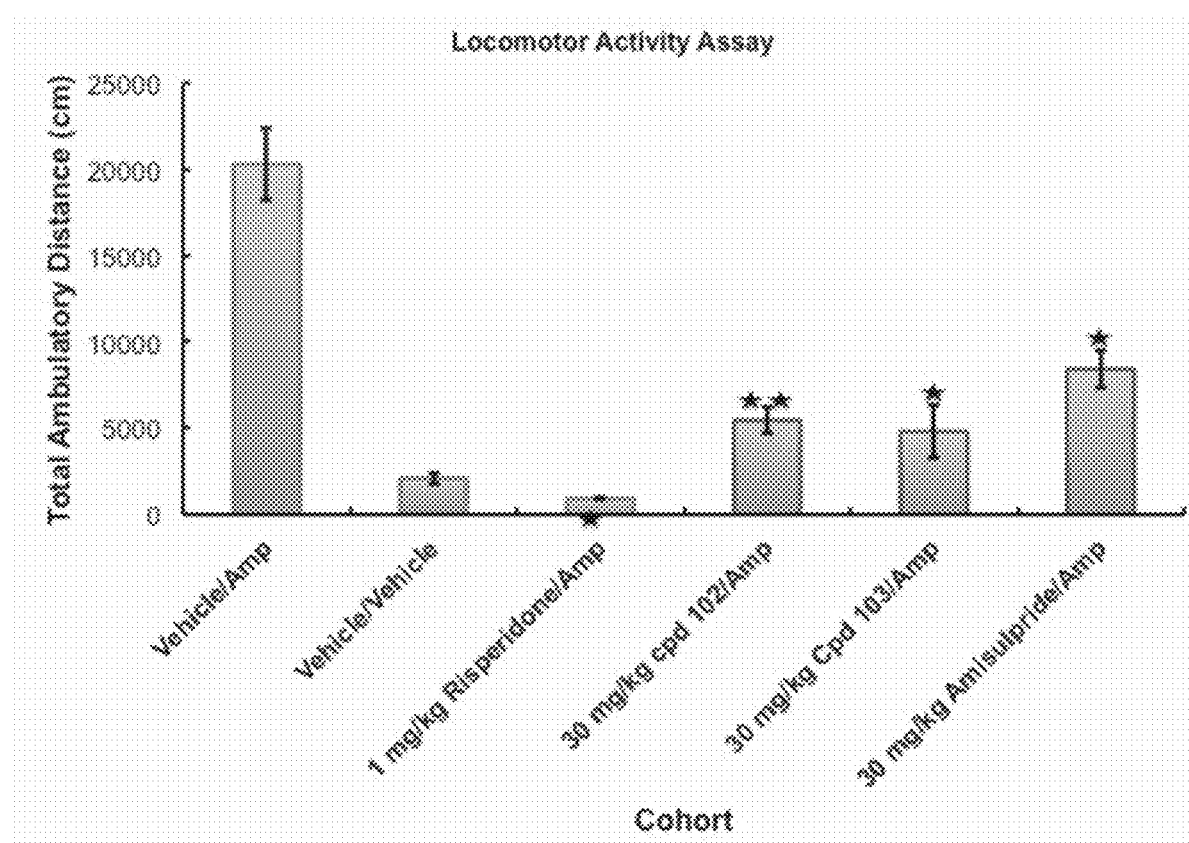
FIG. 2: Total Ambulatory Distance (over 1 hour)±SEM (n=10/group). p<0.05 for all treated groups compared to amphetamine.

In this LMA study in rats, as shown in FIG. 2, the normalized amphetamine hyperactivity of Compound 102 was statistically superior to that of amisulpride (p<0.05), and the normalized amphetamine hyperactivity of Compound 103 was statistically indistinguishable from that of amisulpride (p<0.01).

REFERENCES

The references listed below, and all references cited in the specification are hereby incorporated by reference in their entireties, as if fully set forth herein.
1) H. Y. Meltzer and S. S. Stahl, "The Dopamine Hypothesis of Schizophrenia—A Review," Schizophr. Bull., 1976, 2, 19-76.
2) J. J. Joyce and J. H. Meador-Woodruff, "Linking the Family of D₂ Receptors to Neuronal Circuits in Human Brain: Insights into Schizophrenia," Neuropsychopharmacology, 1997, 16, 1444-1449.
3) S. Wulff, L. Hageman Pinborg, C. Svarer, L. Thorbjørn Jensen, M. Ødegaard Nielsen, P. Allerup, N. Bak, H. Rasmussen, E. Frandsen, E. Rostrup, and B. Yding Glenthøj, "Striatal D₂/3 Binding Potential Values in Drug-Naïve First-Episode Schizophrenia Patients Correlate with Treatment Outcome," Schizophrenia Bulletin, 2015, 41, 1143-1152.
4) B. L. Roth, D. J. Sheffler, and W. K. Kroeze, "Magic Shotguns Versus Magic Bullets: Selectively Non-Selective Drugs for Mood Disorders and Schizophrenia," Nature Reviews Drug Discovery, 2004, 3, 353-359.
5) M. Thominet, J. Acher, and J.-C. Monier, "Derivatives of 4-Amino-5-Alkyl Sulphonyl Orthoamides," U.S. Pat. No. 4,401,822, Filed Oct. 9, 1981 (Issued Aug. 30, 1983).
6) H. Shoemaker, Y. Claustre, D. Fage, L. Rouquier, K. Chergui, O. Curet, A. Oblin, F. Gonon, J. Benavides, and B. Scatton, "Neurochemical Characteristics of Amisulpride, An Atypical Dopamine D2/D3 Receptor Antagonist with Both Presynaptic and Limbic Selectivity," J. Pharmacol. Exp. Ther., 1997, 280, 83-97.
7) A. A. Abbas, P. B. Hedlund, X-P. Huang, T. B. Tran, H. Y. Meltzer, and B. L. Roth, "Amisulpride Is a Potent 5-Ht7 Antagonist: Relevance for Antidepressant Actions In Vivo," Psychopharmacology, 2009, 119-128.
8) S. Jafari, F. Femandez-Enright, and X.-F. Huang, "Structural Contributions of Antipsychtoic Drugs to Their Therapeutic Profiles and Metabolic Side Effects," J. Neurochemistry, 2012, 120, 371-384.
9) J. N. Dos Santos Pereira, S. Tadjerpisheh, M. Abu Abed, A. R. Saadatmand, B. Weksler, I. A. Romero, P.-O. Couraud, J. Brockmöller, and M. V. Tzvetkov, "The Poorly Membrane Permeable Antipsychotic Drugs Amisulpride and Sulpride Are Substrates of the Organic Cation Transporters from the SLC22 Family," The AAPS Journal, 2014, 16, 1247-1258.
10) J. C. Neill, S. Barnes, S. Cook, B. Grayson, N. F. Idris, S. L. McLean, S. Snigdha, L. Rajagopal, and M. K. Harte, "Animal Models of Cognitive Dysfunction and Negative Symptoms of Schizophrenia: Focus on NMDA Receptor Antagonism," Pharmacology & Therapeutics, 2010, 128, 419-432.
11) J. C. Neill, M. K. Harte, P. M. Haddad, E. S. Lydall, and D. M. Dwyer, "Acute and Chronic Effects of Nmda Receptor Antagonists in Rodents, Relevance to Negative Symptoms of Schizophrenia: A Translational Link to Humans," European Neuropsychopharmacology, 2014, 24, 822-835.
12) J. C. Neill, B. Grayson, B. Kiss, I. Gyertyán, P. Ferguson, and N. Adham, "Effects of Cariprazine, A Novel Antipsychotic, On Cognitive Deficit and Negative Symptoms in a Rodent Model of Schizophrenia Symptomatology," European Neuropsychopharmacology, 2016, 26, 3-14.

What is claimed is:
1. A compound having a structure of Formula IA:

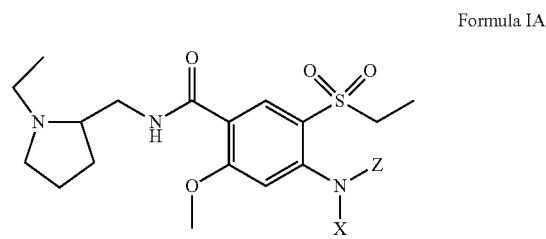

Formula IA pharmaceutically acceptable salts and stereoisomers thereof, wherein:
X and Z are the same or different and independently selected from the group consisting of hydrogen, alkyl, alkenyl, alkynyl, cycloalkyl, cycloalkylalkyl, heterocyclyl, heterocyclylalkyl, aryl, arylalkyl, heteroarylalkyl, and heteroaryl, optionally the alkyl, alkenyl, alkynyl, cycloalkyl, cycloalkylalkyl, heterocyclyl, heterocyclylalkyl, aryl, arylalkyl, heteroarylalkyl, and heteroaryl groups are further substituted with one or more substitution groups selected from the group consisting of halogens, chlorine, bromine, fluorine, amines, hydroxy groups, carboxylic acids, nitro groups, carbonyl, alkyl, and aryl groups; with the proviso that at least one of X and Z is not hydrogen.

2. The compound of claim 1, wherein the compound is a stereoisomer having a structure of Formula IA-S:

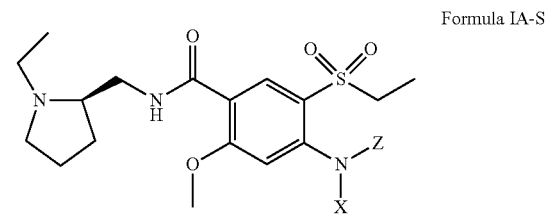

Formula IA-S and pharmaceutically acceptable salts thereof.

3. The compound of claim 1, wherein X and Z are the same or different and independently selected from the group consisting of hydrogen, alkyl, alkenyl, alkynyl, aryl, and heteroaryl, optionally the alkyl, alkenyl, alkynyl, aryl, and heteroaryl groups are further substituted with one or more substitution groups selected from the group consisting of halogens, chlorine, bromine, fluorine, amines, hydroxy groups, carboxylic acids, nitro groups, carbonyl, alkyl, and aryl groups; with the proviso that at least one of X and Z is not hydrogen.

4. The compound of claim 2, wherein X and Z are the same or different and independently selected from the group consisting of hydrogen, alkyl, alkenyl, alkynyl, aryl, and heteroaryl, optionally the alkyl, alkenyl, alkynyl, aryl, and heteroaryl groups are further substituted with one or more substitution groups selected from the group consisting of halogens, chlorine, bromine, fluorine, amines, hydroxy groups, carboxylic acids, nitro groups, carbonyl, alkyl, and aryl groups; with the proviso that at least one of X and Z is not hydrogen.

5. The compound of claim 1, wherein X is H.

6. The compound of claim 5, wherein Z=CH$_3$.

7. The compound of claim 2, wherein X is H.

8. The compound of claim 7, wherein Z=CH$_3$.

9. A pharmaceutical composition comprising a pharmaceutically acceptable carrier and a compound having a structure of Formula IA:

Formula IA pharmaceutically acceptable salts and stereoisomers thereof, wherein:

X and Z are the same or different and independently selected from the group consisting of hydrogen, alkyl, alkenyl, alkynyl, cycloalkyl, cycloalkylalkyl, heterocyclyl, heterocyclylalkyl, aryl, arylalkyl, heteroarylalkyl, and heteroaryl, optionally the alkyl, alkenyl, alkynyl, cycloalkyl, cycloalkylalkyl, heterocyclyl, heterocyclylalkyl, aryl, arylalkyl, heteroarylalkyl, and heteroaryl groups are further substituted with one or more substitution groups selected from the group consisting of halogens, chlorine, bromine, fluorine, amines, hydroxy groups, carboxylic acids, nitro groups, carbonyl, alkyl, and aryl groups; with the proviso that at least one of X and Z is not hydrogen.

10. The pharmaceutical composition of claim 9, wherein the compound is a stereoisomer having a structure of Formula IA-S:

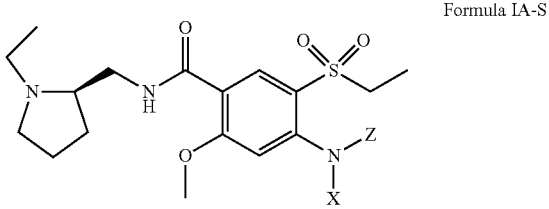

Formula IA-S and pharmaceutically acceptable salts thereof.

11. A method of delivering into the brain of a subject a dopamine and/or serotonin and/or α2 receptor antagonist comprising administering to the subject a therapeutically effective amount of a compound having a structure of Formula IA:

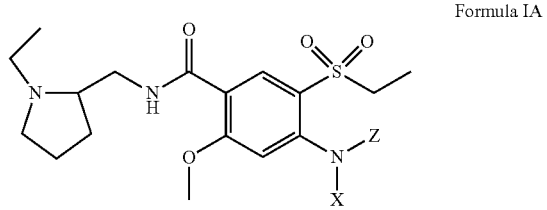

Formula IA pharmaceutically acceptable salts and stereoisomers thereof, wherein:

X and Z are the same or different and independently selected from the group consisting of hydrogen, alkyl, alkenyl, alkynyl, cycloalkyl, cycloalkylalkyl, heterocyclyl, heterocyclylalkyl, aryl, arylalkyl, heteroarylalkyl, and heteroaryl, optionally the alkyl, alkenyl, alkynyl, cycloalkyl, cycloalkylalkyl, heterocyclyl, heterocyclylalkyl, aryl, arylalkyl, heteroarylalkyl, and heteroaryl groups are further substituted with one or more substitution groups selected from the group consisting of halogens, chlorine, bromine, fluorine, amines, hydroxy groups, carboxylic acids, nitro groups, carbonyl, alkyl, and aryl groups; with the proviso that at least one of X and Z is not hydrogen; and the level of the dopamine and/or serotonin and/or α2 receptor antagonist in brain is higher than the level of amisulpride when amisulpride is administered to the subject at a comparable dose.

12. A method of treating one or more conditions selected from the group consisting of depression, bipolar disorder, Tourette's syndrome, Schizoaffective disorder, Parkinson's psychosis, Alzheimer's psychosis, oppositional defiant disorder, personality disorder, childhood schizophrenia, dysthymia, treatment resistant schizophrenia, and chronic fatigue syndrome, the method comprising administering to the subject a therapeutically effective amount of a compound having a structure of Formula IA:

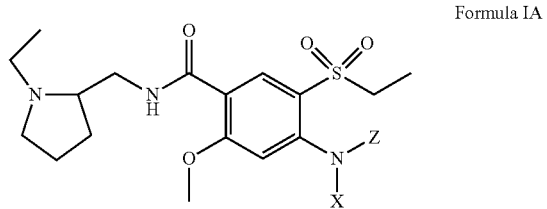

Formula IA pharmaceutically acceptable salts and stereoisomers thereof, wherein:

X and Z are the same or different and independently selected from the group consisting of hydrogen, alkyl, alkenyl, alkynyl, cycloalkyl, cycloalkylalkyl, heterocyclyl, heterocyclylalkyl, aryl, arylalkyl, heteroarylalkyl, and heteroaryl, optionally the alkyl, alkenyl, alkynyl, cycloalkyl, cycloalkylalkyl, heterocyclyl, heterocyclylalkyl, aryl, arylalkyl, heteroarylalkyl, and heteroaryl groups are further substituted with one or more substitution groups selected from the group consisting of halogens, chlorine, bromine, fluorine, amines, hydroxy groups, carboxylic acids, nitro groups, carbonyl, alkyl, and aryl groups; with the proviso that at least one of X and Z is not hydrogen.

13. The method of delivering into the brain of a subject a dopamine and/or serotonin and/or α2 receptor antagonist of claim 11, wherein the compound is a stereoisomer having a structure of Formula IA-S:

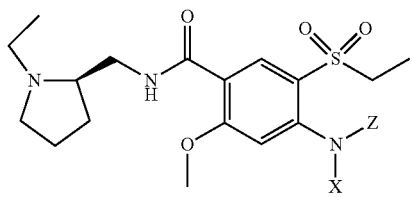

Formula IA-S and pharmaceutically acceptable salts thereof.

14. The compound of claim 1, wherein the compound is a stereoisomer having a structure of Formula IA-R:

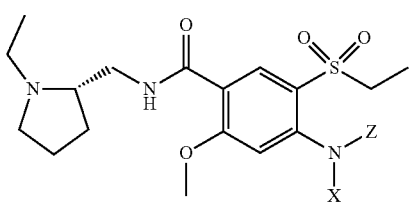

Formula IA-R and pharmaceutically acceptable salts thereof.

15. The compound of claim 14, wherein X and Z are the same or different and independently selected from the group consisting of hydrogen, alkyl, alkenyl, alkynyl, aryl, and heteroaryl, optionally the alkyl, alkenyl, alkynyl, aryl, and heteroaryl groups are further substituted with one or more substitution groups selected from the group consisting of halogens, chlorine, bromine, fluorine, amines, hydroxy groups, carboxylic acids, nitro groups, carbonyl, alkyl, and aryl groups; with the proviso that at least one of X and Z is not hydrogen.

16. The compound of claim 15, wherein X is H.

17. The compound of claim 16, wherein Z=CH$_3$.

18. The pharmaceutical composition of claim 9, wherein the compound is a stereoisomer having a structure of Formula IA-R:

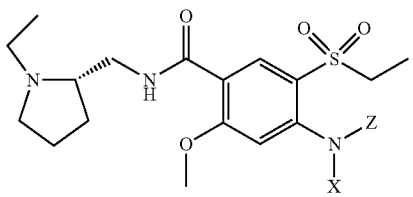

Formula IA-R and pharmaceutically acceptable salts thereof.

19. The method of delivering into the brain of a subject a dopamine and/or serotonin and/or α2 receptor antagonist of claim 11, wherein the compound is a stereoisomer having a structure of Formula IA-R:

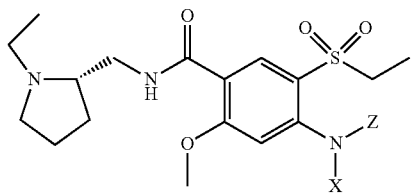

Formula IA-R and pharmaceutically acceptable salts thereof.

20. The method of treating one or more conditions of claim 12, wherein the compound is a stereoisomer having a structure of Formula IA-R:

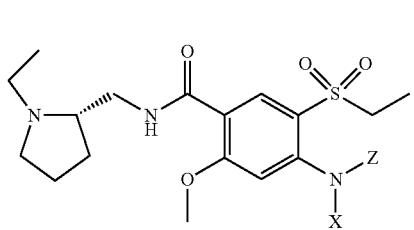

Formula IA-R and pharmaceutically acceptable salts thereof.

21. The method of treating one or more conditions of claim 12, wherein the compound is a stereoisomer having a structure of Formula IA-S:

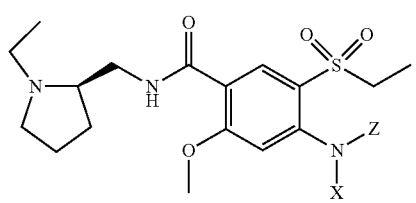

Formula IA-S and pharmaceutically acceptable salts thereof.

* * * * *